US011980632B2

(12) United States Patent
Kweon et al.

(10) Patent No.: US 11,980,632 B2
(45) Date of Patent: May 14, 2024

(54) ANTIVIRAL COMPOSITION CONTAINING FUCOSYLLACTOSE AS ACTIVE INGREDIENT

(71) Applicant: ADVANCED PROTEIN TECHNOLOGIES CORP., Suwon-si (KR)

(72) Inventors: Dae Hyuk Kweon, Seoul (KR); Seok Oh Moon, Gwacheon-si (KR); Jung Hee Moon, Suwon-si (KR); Chul Soo Shin, Suwon-si (KR); Jong Won Yoon, Seongnam-si (KR); Seon Min Jeon, Daegu (KR); Young Ha Song, Yongin-si (KR); Jong Gil Yoo, Suwon-si (KR)

(73) Assignee: ADVANCED PROTEIN TECHNOLOGIES CORP., Suwon-si (KR)

( * ) Notice: Subject to any disclaimer, the term of this patent is extended or adjusted under 35 U.S.C. 154(b) by 0 days.

(21) Appl. No.: 17/993,760

(22) Filed: Nov. 23, 2022

(65) Prior Publication Data

US 2023/0114000 A1     Apr. 13, 2023

Related U.S. Application Data

(63) Continuation of application No. PCT/KR2021/018556, filed on Dec. 8, 2021.

(30) Foreign Application Priority Data

Dec. 11, 2020   (KR) .......................... 10-2020-0173106

(51) Int. Cl.
*A61K 31/702*      (2006.01)
*A61P 31/14*       (2006.01)

(52) U.S. Cl.
CPC ............ *A61K 31/702* (2013.01); *A61P 31/14* (2018.01)

(58) Field of Classification Search
None
See application file for complete search history.

(56) References Cited

U.S. PATENT DOCUMENTS

2016/0220594 A1*  8/2016  Buck ................... A61K 31/702
2020/0022996 A1   1/2020  Buck et al.

FOREIGN PATENT DOCUMENTS

| CN | 110100905 A     | 8/2019  |
| KR | 10-1793195 B1   | 11/2017 |
| KR | 10-2019-0126350 A | 11/2019 |
| KR | 10-2020-0096770 A | 8/2020  |
| KR | 10-2021-0116783 A | 9/2021  |

OTHER PUBLICATIONS

Pitt, J., et al. "Safety assessment of the biotechnologically produced human-identical milk oligosaccharide 3-Fucosyllactose (3-FL)." Food and Chemical Toxicology 134 (2019): 110818.*
Zhang, Lei, and Youwei Zhang. "Influenza viral infection is a high-risk factor for developing coronavirus disease 2019 (COVID-19)." (2020).*
Ling Xiao, et al. "Human Milk Oligosaccharide 2'-Fucosyllactose Improves Innate and Adaptive Immunity in an Influenza-Specific Murine Vaccination Model", Frontiers in Immunology, Mar. 2018, pp. 1-17, vol. 9, Article 452.
Geralyn Duska-McEwen, et al., "Human Milk Oligosaccharides Enhance Innate Immunity to Respiratory Syncytial Virus and Influenza in Vitro", Food and Nutrition Sciences, Scientific Research, 2014, vol. 5, pp. 1387-1398.
Vassilis Triantis, et al., "Immunological Effects of Human Milk Oligosaccharides", Frontiers in Pediatrics, Jul. 2018, pp. 1-15, vol. 6, Article 190.
Xiuyuan Ou, et al., "Characterization of spike glycoprotein of SARS-COV-2 on virus entry and its immune cross-reactivity with SARS-CoV", Nature Communications, 2020, pp. 1-12, 11:1620 | https://doi.org/10.1038/s41467-020-15562-9 |www.nature.com/naturecommunications.
Jianhui Nie, et al., "Quantification of SARS-CoV-2 neutralizing antibody by a pseudotyped virus-based assay", Nature Protocols, Nov. 2020, pp. 3699-3715, vol. 15.
Jose Manuel Condor Capcha, et al., "Generation of SARS-CoV-2 Spike Pseudotyped Virus for Viral Entry and Neutralization Assays: A 1-Week Protocol", Frontiers in Cardiovascular Medicine, Jan. 2021, pp. 1-12, vol. 7, Article 618651.
Fabio Lisi, et al., "Nitric Oxide to Fight Viral Infections", ESSAY, Advanced Science News, 2021, pp. 1-9, vol. 8.
Mark R. Garren, et al., "Nitric oxide and viral infection: Recent developments in antiviral therapies and platforms", ELSEVIER, Applied Materials Today, 2021, pp. 1-17, 100887.
Vasily Morozov, et al., "Human Milk Oligosaccharides as Promising Antivirals", Molecular Nutrition Food Research, 2018, pp. 1-14, vol. 62.
International Search Report for PCT/KR2021/018556 dated Mar. 14, 2022.

(Continued)

*Primary Examiner* — Patrick T Lewis
(74) *Attorney, Agent, or Firm* — Sughrue Mion, PLLC

(57) ABSTRACT

Disclosed is fucosyllactose having antiviral activity and inhibitory activity against viral infection, and a method for preventing or treating a viral infection by administering a composition including fucosyllactose as an active ingredient to a subject in need thereof. It was found that 2'-fucosyllactose and 3-fucosyllactose, which are human milk oligosaccharides (HMOs), have antiviral activity, and in particular, 3-fucosyllactose in vitro and in vivo exhibits much higher antiviral activity and inhibitory activity against viral infection compared to 2'-fucosyllactose and is thus useful as an antiviral agent.

2 Claims, 7 Drawing Sheets

(56) References Cited

OTHER PUBLICATIONS

Korean Office Action for Korean Application No. 10-2021-0175054 dated Feb. 3, 2022, 13 pages.

* cited by examiner

ANTIVIRAL COMPOSITION CONTAINING FUCOSYLLACTOSE AS ACTIVE INGREDIENT

CROSS-REFERENCE TO RELATED APPLICATIONS

This application is a Bypass Continuation of PCT/KR2021/018556 filed on Dec. 8, 2021, which is based on and claims priority from Korean Patent Application No. 10-2020-0173106 filed on Dec. 11, 2020, the entire disclosures of which are incorporated herein by reference.

BACKGROUND OF THE INVENTION

Field of the Invention

The present invention relates to fucosyllactose having antiviral activity and inhibitory activity against viral infection, and a method for preventing or treating a viral infection by administering a composition including fucosyllactose as an active ingredient to a subject in need thereof.

Description of the Related Art

A virus means a toxic substance in Latin and is a group of infectious pathogenic particles that pass through a bacterial filter paper (0.22 um). A virus may be classified into bacteriophages, plant viruses, and animal viruses depending on the type of host cells and may be classified into DNA viruses and RNA viruses depending on the type of nucleic acid. Recently, various viral diseases such as swine flu, avian influenza, and foot-and-mouth disease have caused great social problems and thus concerns about effective countermeasures for viral diseases have aroused great social interest. The current best way to prevent viral diseases is vaccination, but effectiveness of vaccines raised as an important issue due to the production of many viral serotypes (subtypes). The development and dissemination of inhibitors for preventing virus that can solve the problems of vaccines are important. For this purpose, the discovery and development of prophylactic agents that increase the immunity of individual animals by stimulating the in vivo innate immune system, which is the initial defense system against viruses, may be a key method for developing drugs.

Influenza virus is divided into four types, namely, influenza viruses A, B, C, and D. Only influenza C virus only infects humans, but is not contagious, influenza D virus does not cause disease in humans, and influenza A and B virus are strong viruses that mainly occur in winter and infect the human respiratory system and thus cause systemic symptoms. Representative antiviral agents that inhibit the proliferation of influenza virus include amantadine and rimantadine. These two antiviral agents are effective only for serotype A influenza virus and are ineffective for serotype B influenza virus having no M2 proteins. In addition, amantadine and rimantadine have been found to have a drawback in that mutant viruses that do not affect the ion channel function of influenza virus M2 proteins are readily formed. In order to reduce this drawback, Zanamivir and Oseltamivir have been developed as effective antiviral agents against all 16 serotype A influenza viruses and serotype B influenza viruses. However, Zanamivir is disadvantageously administered by inhalation and intravenous administration and Oseltamivir may be administered orally, but have been recently reported to have drawbacks of emergence of resistant viruses and side effects such as vomiting and dizziness upon oral administration.

Coronaviruses are enveloped viruses having single-stranded positive RNA genomes and have been isolated from a variety of animals including humans since they were first found in 1937. Coronaviruses may be divided into four groups. Among them, alpha-coronavirus and beta-coronavirus mainly infect mammals, while gamma-coronavirus and delta-coronavirus infect birds. However, recently, there has been a confirmed case of infection of pigs with delta-coronavirus. Coronaviruses may be propagated heterogeneously. Representative examples include the SARS coronavirus that caused severe acute respiratory syndrome that was prevalent worldwide in 2003 and the MERS coronavirus that spread in Korea in 2015. As described above, coronaviruses may be propagated heterogeneously and novel coronaviruses derived from bats may spread to humans and cause great problems. Therefore, there is an urgent need for development of effective antiviral agents to detect novel bat-derived coronaviruses. Non-specific antiviral agents that have shown efficacy in clinical practice include type I interferon and ribavirin, but have been reported to have antiviral effects only in the early stages of infection. In response to the increasing need for development, therapeutic agents for MERS-CoV and SARS-CoV have recently attracted attention (A. Zumla et. al, Nature Reviews Drug Discovery, 15:327-347, 2016). However, there are currently neither approved therapeutic agents nor vaccines in both Korea and other countries, and a system for evaluating developed substances has not been established. Therefore, there is an urgent need for development of a system for evaluating the efficacy of the substances.

Therapeutic agents for viral infections developed to date include amantadine- or rimantadine-type M2 ion channel inhibitors and oseltamivir—(trade name: Tamiflu) or zanamivir (trade name: Relenza)-type neuraminidase inhibitors, but these therapeutic agents have a problem of limited effectiveness. That is, it is known that variant viruses resistant to amantadine- or rimantadine-derived compounds are rapidly produced, H5N1-type influenza viruses detected in some areas are resistant to amantadine- or rimantadine-based compounds, and influenza B virus is insensitive to amantadine derivatives. In addition, it is known that the number of viruses resistant to oseltamivir- or zanamivir-derived compounds also increases, and these resistant viruses frequently occur in children.

Meanwhile, human breast milk contains 200 or more kinds of human milk oligosaccharides (HMOs) having different structures, which are present at a considerably higher concentration (5 to 15 g/L) than in other mammals. These HMOs have essential functions in infants and toddlers, such as a prebiotic effect, an effect of inhibiting intestinal adhesion of pathogens, and an effect of regulating the immune regulation system.

The related art includes Korean Patent Publication No. 10-2020-009677, and research related to viruses disclosed in papers such as Ou X, Liu Y, Lei X et al., 2020, Characterization of spike glycoprotein of SARS-CoV-2 on virus entry and its immune cross-reactivity with SARS-CoV, Nat Commun11, 1620, Nie J, Li Q, Wu J et al., 2020, Quantification of SARS-CoV-2 neutralizing antibody by a pseudotyped virus-based assay, Nat Protoc 15, 3699-3715, and Condor Capcha J M, Lambert G, Dykxhoorn D M et al., 2020, Generation of SARS-CoV-2 Spike Pseudotyped Virus for Viral Entry and Neutralization Assays; A 1-Week Protocol, Front Cardiovasc Med 7, 618651.

SUMMARY OF THE INVENTION

Therefore, the present invention has been made in view of the above problems, and it is one object of the present invention to provide an antiviral composition.

It is another object of the present invention to provide a pharmaceutical composition for preventing or treating viral infections.

It is another object of the present invention to provide a food composition for preventing or ameliorating viral infection.

It is another object of the present invention to provide a veterinary pharmaceutical composition for preventing or treating viral infections.

It is another object of the present invention to provide a prebiotic composition for preventing or ameliorating viral infections.

It is another object of the present invention to provide a feed or feed additive composition for preventing or ameliorating viral infections.

In accordance with the present invention, the above and other objects can be accomplished by the provision of an antiviral composition containing fucosyllactose as an active ingredient.

Meanwhile, in the antiviral composition, the fucosyllactose is preferably 2'-fucosyllactose (2'-FL) or 3-fucosyllactose (3-FL).

Meanwhile, in the antiviral composition, the virus is preferably at least one virus selected from the group consisting of Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, Picornaviridae and Herpesviridae.

Meanwhile, in the antiviral composition, the virus is preferably influenza virus or coronavirus.

In accordance with another aspect of the present invention, provided is a pharmaceutical composition for preventing or treating a viral infection containing fucosyllactose as an active ingredient.

Meanwhile, in the pharmaceutical composition, the fucosyllactose is preferably 2'-fucosyllactose or 3-fucosyllactose.

Meanwhile, in the pharmaceutical composition, the viral infection is preferably an infection with at least one virus selected from the group consisting of Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, Picornaviridae and Herpesviridae.

Meanwhile, in the pharmaceutical composition, the viral infection is preferably an infection with influenza virus or coronavirus.

In accordance with another aspect of the present invention, provided is a food composition for preventing or ameliorating a viral infection containing fucosyllactose as an active ingredient.

Meanwhile, in the food composition, the fucosyllactose is preferably 2'-fucosyllactose or 3-fucosyllactose.

Meanwhile, in the food composition, the viral infection is preferably an infection with at least one virus selected from the group consisting of Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, Picornaviridae and Herpesviridae.

Meanwhile, in the food composition, the food composition is preferably an infant formula.

In accordance with another aspect of the present invention, provided is a veterinary pharmaceutical composition for preventing or treating a viral infection containing fucosyllactose as an active ingredient.

Meanwhile, in the veterinary pharmaceutical composition, the fucosyllactose is preferably 2'-fucosyllactose or 3-fucosyllactose.

In accordance with another aspect of the present invention, provided is a prebiotic composition for preventing or ameliorating a viral infection containing fucosyllactose as an active ingredient.

Meanwhile, in the prebiotic composition, the fucosyllactose is preferably 2'-fucosyllactose or 3-fucosyllactose.

In accordance with another aspect of the present invention, provided is a feed or feed additive composition for preventing or ameliorating a viral infection containing fucosyllactose as an active ingredient.

Meanwhile, in the feed or feed additive composition, the fucosyllactose is preferably 2'-fucosyllactose or 3-fucosyllactose.

In another embodiment, the present disclosure provides a method for preventing or treating a viral infection, comprising administering a composition comprising fucosyllactose as an active ingredient to a subject in need thereof. In one embodiment, the fucosyllactose is 2'-fucosyllactose or 3-fucosyllactose. In another embodiment, the viral infection is an infection with at least one virus selected from the group consisting of Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, Picornaviridae and Herpesviridae. In some embodiment, the viral infection is an infection with influenza virus or coronavirus.

BRIEF DESCRIPTION OF THE DRAWINGS

The above and other objects, features, and other advantages of the present invention will be more clearly understood from the following detailed description taken in conjunction with the accompanying drawings, in which.

DETAILED DESCRIPTION OF THE INVENTION

Figure 1:
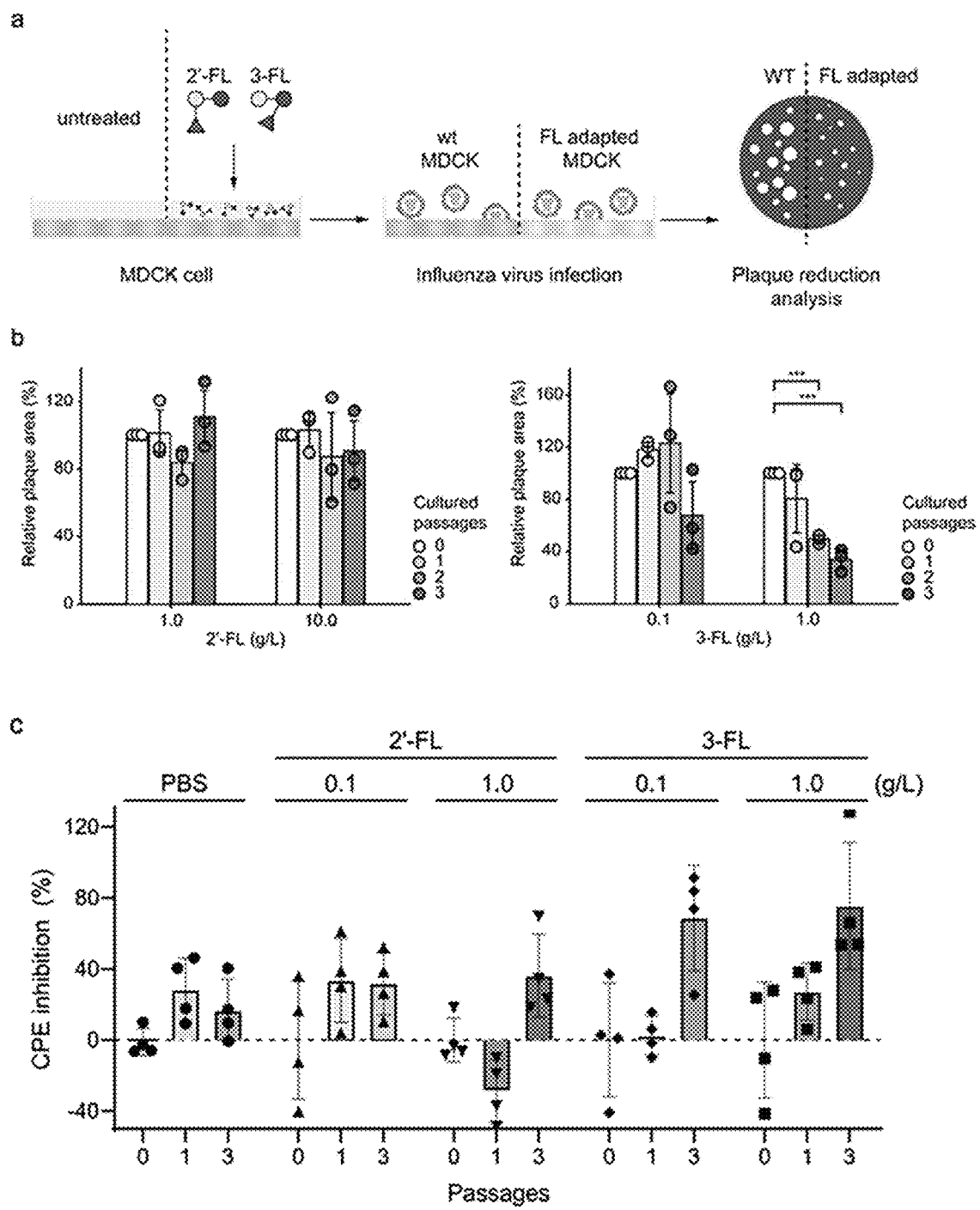
FIG. 1 is a schematic diagram illustrating a process of an experiment including treating MDCK cell culture medium with fucosyllactose, performing culture for 0 to 3 passages and then performing plaque reduction assay to determine the antiviral effect of fucosyllactose on influenza virus infection (a), the result thereof (b) and the result using a cytopathic effect reduction assay (c). In this case, 2'-FL represents 2'-fucosyllactose, 3-FL represents 3-fucosyllactose, and the same applies to the drawings below.

Hereinafter, embodiments of the present invention will be described in detail with reference to the accompanying drawings. However, the following embodiments are provided merely for illustration of the present invention. Detailed descriptions of technologies and configurations well-known to those skilled in the art will be omitted when they may obscure the subject matter of the present invention, and are not intended to limit the invention. Various modifications and applications of the present invention are possible within the scope of the claims described later and equivalents derived therefrom.

In addition, the terminology used herein is used to accurately describe preferred embodiments, and may be changed according to intentions or customs of users or operators. Accordingly, the definitions of the terminology should be understood based on the content throughout the specification. It will be further understood that terms such as "comprises" and the like, when used in this specification, specify the presence of other components, but do not preclude the presence or addition of other components unless otherwise mentioned.

Unless otherwise defined, all technical terms used herein have the same meanings as generally understood by those skilled in the art to which the present invention pertains. In addition, preferred methods and samples described herein and equivalents thereto fall within the scope of the present invention. The disclosures of all publications mentioned herein are incorporated herein by reference in their entireties.

In one aspect, the present invention provides an antiviral composition containing fucosyllactose as an active ingredient.

In an embodiment, the fucosyllactose corresponds to human milk oligosaccharides (HMOs), and is 2'-fucosyllactose (2'-FL) or 3-fucosyllactose (3-FL), or 2'-fucosyllactose (2'-FL) and 3-fucosyllactose (3-FL).

In one embodiment, 2'-fucosyllactose (2'-FL) may have an antiviral effect that acts directly on the virus, and 3-fucosyllactose may have the effect of imparting resistance to viruses through virus infection pretreatment. Therefore, when 2'-fucosyllactose and 3-fucosyllactose are administered in combination, both resistance to viruses and direct antiviral activity can be obtained.

In an embodiment, the virus is preferably at least one virus selected from the group consisting of Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, Picornaviridae and Herpesviridae, more preferably, influenza virus or corona virus.

In another aspect, the present invention provides a pharmaceutical composition for preventing or treating a viral infection containing fucosyllactose as an active ingredient.

In an embodiment, the fucosyllactose is preferably 2'-fucosyllactose or 3-fucosyllactose, or 2'-fucosyllactose and 3-fucosyllactose.

In one embodiment, 2'-fucosyllactose (2'-FL) may have an antiviral effect that acts directly on the virus, and 3-fucosyllactose has the effect of imparting resistance to viruses through virus infection pretreatment.

In an embodiment, the viral infection is preferably an infection with at least one virus selected from the group consisting of Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, Picornaviridae and Herpesviridae, more preferably, influenza virus or corona virus.

As used herein, the term "treatment" refers to activity of ameliorating or positively changing the symptoms of an infectious disease caused by a viral infection. Those skilled in the art to which the present invention pertains can appreciate exact criteria of diseases against which the composition of the present application is effective, and determine the extent of amelioration, improvement, and treatment with reference to data provided by the Korean Medical Association, etc.

As used herein, the term "prevention" refers to prevention of the onset, recurrence, or transmission of a disease or disorder, or one or more symptoms caused by the disease or disorder, and includes prophylactic treatment for potential candidates.

The composition of the present invention may be prepared in the form of a pharmaceutical composition for preventing or treating inflammatory diseases further containing an appropriate carrier, excipient, or diluent commonly used in the preparation of pharmaceutical compositions, and the carrier may be a natural carrier. Specifically, the pharmaceutical composition may be prepared into an oral formulation such as a powder, granule, tablet, capsule, suspension, emulsion, syrup, or aerosol, or a formulation such as an external preparation, suppository, or a sterile injection solution in accordance with a conventional method. In the present invention, the pharmaceutical composition may contain at least one selected from the group consisting of various carriers, excipients and diluents that may be contained in the pharmaceutical composition.

The content of the fucosyllactose in the pharmaceutical composition of the present invention is, for example, 0.0001 to 40% by weight, or 0.01 to 10% by weight, based on the total weight of the pharmaceutical composition, but is not limited thereto.

The therapeutically effective amount of the composition of the present invention may vary depending on several factors, for example, the administration method, the target site, the condition of the patient, and the like. Therefore, the dosage when used in the human body should be determined as an appropriate amount in consideration of both safety and efficacy. The amount for use in humans may be estimated based on effective amounts determined through animal experimentation. Considerations for determining the effective amount are disclosed, for example, in Hardman and. Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The pharmaceutical composition of the present invention may be administered in a pharmaceutically effective amount. As used herein, the term "pharmaceutically effective amount" means an amount sufficient to treat or prevent a disease at a reasonable benefit/risk ratio applicable to pharmaceutical (medical) treatment, while causing no side effects. The effective dosage is determined depending on factors including the state of health of the patient, the type of the infection, severity, drug activity, drug sensitivity, administration method, administration time, administration route, excretion rate, treatment period, drugs used in combination with or concurrently with the composition of the present invention, and other factors well known in the pharmaceutical field. The composition of the present invention may be administered as a single therapeutic agent or in combination with other therapeutic agents, sequentially or simultaneously with conventional therapeutic agents, and in one or multiple doses. Taking into consideration these factors, it is important to administer the composition in the minimum amount sufficient to achieve maximum efficacy without side effects, which can be easily determined by those skilled in the art.

The composition of the present invention may further contain a carrier, diluent, or excipient commonly used in biological agents, or a combination of two or more thereof. Any pharmaceutically acceptable carrier may be used without particular limitation, as long as it is suitable for in-vivo delivery of the composition. For example, the pharmaceutically acceptable carrier may be a compound, saline, sterile water, Ringer's solution, buffered saline, dextrose solution, maltodextrin solution, glycerol, ethanol, or a combination of two or more of these components disclosed in Merck Index, 13th ed., Merck & Co. Inc. If necessary, other conventional additives such as antioxidants, buffers, and bacteriostats may be added. In addition, the composition may be prepared into an injectable formulation, such as an aqueous solution, suspension, or emulsion, or a pill, a capsule, a granule, or a tablet by further adding a diluent, dispersant, surfactant, binder, or lubricant. Furthermore, the composition may be preferably formulated according to the corresponding disease or component using an appropriate method in the art or a method disclosed in Remington's Pharmaceutical Science (Mack Publishing Company, Easton PA, $18^{th}$ edition, 1990).

As used herein, the term "pharmaceutically acceptable" means a property of being non-toxic to cells or humans exposed to the composition.

The pharmaceutical composition of the present invention may further contain a pharmaceutically acceptable additive. Preferred pharmaceutically acceptable additives include starch, gelatinized starch, microcrystalline cellulose, lactose, povidone, colloidal silicon dioxide, calcium hydrogen phosphate, lactose, mannitol, syrup, gum arabic, pregelatinized starch, corn starch, powdered cellulose, hydroxypropyl cellulose, Opadry, sodium starch glycolate, lead carnauba, synthetic aluminum silicate, stearic acid, magnesium stearate, aluminum stearate, calcium stearate, sucrose, dextrose, sorbitol, talc, and the like. The pharmaceutically acceptable additive according to the present invention is preferably present in an amount of 0.1 to 90 parts by weight based on the weight of the composition, but is not limited thereto.

As used herein, the term "administration" means supplying a predetermined substance to a patient using any suitable method, and may be classified into parenteral administration (e.g., using an intravenous, subcutaneous, intraperitoneal, or topical injection formulation) and oral administration depending on the intended method, and the dosage may vary greatly depending on the patient's weight, age, gender, state of health, diet, administration time, administration method, excretion rate, and severity of disease.

The dosage of the pharmaceutical composition of the present invention may be determined by those skilled in the art in consideration of the purpose of use, the severity of the disease, the age, weight, gender and disease history of the patient, or the type of substance used as an active ingredient. For example, the pharmaceutical composition of the present invention may be administered in an amount from about 0.1 ng/kg to about 100 mg/kg, preferably from 1 ng/kg to about 10 mg/kg in an adult. The administration frequency of the composition of the present invention is not particularly limited and the pharmaceutical composition may be administered once a day or several times a day, divided into multiple doses. The dosage does not limit the scope of the present invention in any way.

The administration of the pharmaceutical composition for treating viral infection of the present invention may be performed through any general route as long as it is capable of reaching the target tissue. The administration of the pharmaceutical composition of the present invention may be achieved through intraperitoneal administration, intravenous administration, intramuscular administration, subcutaneous administration, intradermal administration, oral administration, intranasal administration, intrapulmonary administration, rectal administration, or the like, but is not limited thereto. However, when administered orally, the fucosyllactose may be denatured or destroyed by gastric acid, so the oral composition should be formulated so as to be coated with an active agent or to protect the fucosyllactose from degradation in the stomach. In addition, the composition may be administered by any device capable of delivering the active substance to a target cell.

In another aspect, the present invention is directed to a method of treating a viral infection including administering the pharmaceutical composition in a pharmaceutically effective amount to a subject having or likely to develop a viral infection caused by infection with a virus.

As used herein, the term "subject" encompasses mammals including humans, mice, livestock, and the like, farmed fish, and the like which have or are likely to develop a viral infection caused by infection with a virus, without limitation thereto.

In another aspect, the present invention is directed to a composition for inhibiting a viral infection containing the fucosyllactose according to the present invention.

In another aspect, the present invention is directed to a food composition for treating or ameliorating a viral infection containing fucosyllactose as an active ingredient.

In an embodiment, the fucosyllactose is 2'-fucosyllactose or 3-fucosyllactose, or 2'-fucosyllactose and 3-fucosyllactose, most preferably 3-fucosyllactose.

In an embodiment, the viral infection is an infection with at least one virus selected from the group consisting of Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, Picornaviridae and Herpesviridae, more preferably, influenza virus or coronavirus.

In an embodiment, the food composition is an infant formula.

When the composition of the present invention is used as a food composition, it may be added alone or used in combination with other foods or food ingredients, and may be appropriately used according to a conventional method. The composition of the present invention includes a cytologically acceptable food supplement, in addition to the active ingredient. The amount of the active ingredient that is mixed may be appropriately determined depending on the application (prevention, health or therapeutic treatment).

As used herein, the term "food supplement" refers to a component that may be supplementally added to food and is added to prepare health functional foods of each formulation, and may be appropriately select by those skilled in the art. Examples of the food supplement include, but are not limited to, various nutrients, vitamins, minerals (electrolytes), flavoring agents such as synthetic and natural flavoring agents, coloring agents, fillers, pectic acid and salts thereof, alginic acid and salts thereof, organic acids, protective colloidal thickeners, pH adjusters, stabilizers, preservatives, glycerin, alcohols, carbonizing agents used in carbonated beverages, and the like.

Examples of the food composition to which fucosyllactose may be added include various foods, beverages, gum, tea, vitamin complexes, health functional foods, and the like.

In addition, fucosyllactose may be added to food or beverage to prevent viral infection. In this case, the amount of fucosyllactose in the food or beverage may be added in an amount of 0.01 to 15% by weight of the total food weight and the amount of fucosyllactose may be 0.02 to 5 g, preferably 0.3 to 1 g with respect to 100 ml of the health beverage composition.

The health functional beverage composition of the present invention has no particular limitation to other ingredients, except that it contains the fucosyllactose as an essential ingredient at the predetermined ratio, and may contain additional ingredients such as various flavoring agents or natural carbohydrates like a conventional beverage. Examples of the natural carbohydrates include monosaccharides such as glucose and fructose, disaccharides such as maltose and sucrose, polysaccharides such as conventional sugars such as dextrin and cyclodextrin, and sugar alcohols such as xylitol, sorbitol, and erythritol. Useful flavoring agents other than those mentioned above include natural flavoring agents such as thaumatin, stevia extracts, such as rebaudioside A and glycyrrhizin, and synthetic flavoring agents such as saccharin and aspartame and the like. The content of the natural carbohydrate is generally about 1 to 20 g, preferably about 5 to 12 g with respect to 100 ml of the composition of the present invention.

Further, the fucosyllactose of the present invention may contain various nutrients, vitamins, minerals (electrolytes), flavoring agents such as synthetic and natural flavoring agents, coloring agents, fillers, pectic acid and salts thereof, alginic acid and salts thereof, organic acids, protective colloidal thickeners, pH adjusters, stabilizers, preservatives, glycerin, alcohols, carbonizing agents used in carbonated beverages, and the like. In addition, the fucosyllactose of the present invention may contain natural fruit juice and pulp for the production of fruit juice beverages and vegetable beverages. This component may be used independently or in combination. In this case, although the proportion of the additive is not very important, the additive is generally selected in the range of 0 to about 20 parts by weight with respect to 100 parts by weight of the fucosyllactose of the present invention.

In addition, the food composition of the present invention includes health functional food. The term "health functional food" means food manufactured and processed in the form of tablets, capsules, powders, granules, liquids and pills using raw materials or ingredients useful for the human body, and the term "functional" means intake of food with the goal of obtaining beneficial effects for health such as regulation of nutrients appropriate for structures and functions of the human body or physiological effects. In addition, the health functional food according to the present invention may also be prepared in the form of a formulation recognized as a health functional food without limitation. The health functional food of the present invention may be prepared in any of various types of formulations and may be taken as a supplement to enhance the effect of therapeutic agents for autoimmune diseases unlike general drugs due to advantages of not causing side effects that may occur during long-term administration of drugs due to the use of plants as raw materials, and of having excellent portability.

In addition, there is no limitation on the type of health food in which the composition of the present invention may be used. In addition, the composition containing the fucosyllactose according to the present invention as an active ingredient may be prepared by mixing known additives with other suitable auxiliary ingredients that may be contained in health functional foods depending on the selection of those skilled in the art. Examples of the health food, to which the composition may be added, include meat, sausage, bread, chocolate, candy, snacks, confectionery, pizza, ramen, other noodles, gums, dairy products including ice cream, various soups, beverages, tea, drinks, alcoholic beverages, vitamin complexes and the like, and the health food may be prepared by adding the fucosyllactose according to the present invention as a main component to juice, tea, jelly or juice.

Since the composition of the present invention is prepared from natural substances, it has fewer side effects compared to general synthetic compounds even when used as a pharmaceutical composition or a food composition and is safely used for pharmaceutical compositions and health functional foods.

In another aspect, the present invention is directed to a veterinary pharmaceutical composition for preventing or treating a viral infection containing fucosyllactose as an active ingredient.

In an embodiment, the fucosyllactose is 2'-fucosyllactose or 3-fucosyllactose, or 2'-fucosyllactose and 3-fucosyllactose, most preferably, 3-fucosyllactose.

In an embodiment, the virus is preferably at least one virus selected from the group consisting of Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, Picornaviridae and Herpesviridae, more preferably, influenza virus or corona virus.

Meanwhile, the veterinary pharmaceutical composition according to the present invention may be formulated in accordance with a method well-known in the art to provide rapid, sustained or delayed release of the active ingredient after administration to a mammal. The veterinary pharmaceutical composition of the present invention may be prepared as an oral formulation such as a powder, granule, tablet, capsule, suspension, emulsion, syrup, or aerosol, an external preparation, suppository, or sterile injection solution.

When the veterinary pharmaceutical composition according to the present invention is prepared as the formulation as described above, ordinary diluents or excipients such as fillers, extenders, binders, wetting agents, disintegrants, and surfactants may be used. Solid preparations for oral administration may include tablets, pills, powders, granules, capsules, and the like, and the solid preparations may be prepared by mixing the fucosyllactose with at least one excipient, for example, starch, calcium carbonate, sucrose, lactose or gelatin.

In addition to simple excipients, lubricants such as magnesium stearate and talc may also be used. Liquid formulations for oral administration include suspensions, solutions, emulsions, syrups and the like, and various excipients such as wetting agents, sweetening agents, fragrances, preservatives, and the like, in addition to water and liquid paraffin, which are commonly used simple diluents, may be included.

Formulations for parenteral administration may include sterile aqueous solutions, non-aqueous solutions, suspensions, emulsions, lyophilizates, suppositories, and the like. Non-aqueous solvents or suspensions may include propylene glycol, polyethylene glycol, vegetable oils such as olive oil, and injectable esters such as ethyl oleate. The base of the suppository may be Witepsol, macrogol, Tween 61, cacao butter, laurin, glycerogelatin, or the like.

The veterinary pharmaceutical composition of the present invention may be administered in a pharmaceutically effective amount. As used herein, the term "pharmaceutically effective amount" means an amount sufficient to treat or prevent a disease at a reasonable benefit/risk ratio applicable to pharmaceutical (medical) treatment, while causing no side effects. The effective dosage is determined depending on factors including the state of health of the patient, the type of the ulcers, severity, drug activity, drug sensitivity, administration method, administration time, administration route, excretion rate, treatment period, drugs used in combination with or concurrently with the composition of the present invention, and other factors well known in the pharmaceutical field.

In another aspect, the present invention is directed to a prebiotic composition for preventing or ameliorating a viral infection containing fucosyllactose as an active ingredient.

In an embodiment, the fucosyllactose is 2'-fucosyllactose or 3-fucosyllactose, or 2'-fucosyllactose and 3-fucosyllactose, most preferably 3-fucosyllactose.

In another aspect, the present invention is directed to a feed or feed additive composition for preventing or ameliorating a viral infection containing fucosyllactose as an active ingredient.

In an embodiment, the fucosyllactose is 2'-fucosyllactose or 3-fucosyllactose, or 2'-fucosyllactose and 3-fucosyllactose, most preferably 3-fucosyllactose.

In an embodiment, the viral infection is an infection with at least one virus selected from the group consisting of Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, Picornaviridae and Herpesviridae, more preferably, influenza virus or coronavirus.

In the feed additive composition according to the present invention, the feed has a known composition generally used for livestock breeding and includes all commercially available general feeds. The feed may include, but is not limited to, grains, plant protein feed, animal protein feed, sugars and dairy products. Examples of the feed include rice bran, corn, soybean meal, soybean, sorghum, rice, barley, wheat, oat, rye, millet, buckwheat, triticale, sweet potato, tapioca, bran, malt bran, soybean hull, corn bran, malt root, starch meal, coffee meal, silkworm feces, seaweed meal, cottonseed meal, rapeseed meal, canola wheat, linseed meal, squash gourd, flax meal, sunflower seed meal, peanut meal, palm meal, corn gluten, alcoholic meal, corn germ meal, red pepper meal, lupine seeds, fish meal, feather meal and meat meal.

In the feed additive composition according to the present invention, the feed additive is a general feed additive, for example, a feed additive for specific application, such as salts, bone powders, calcium phosphate, mineral mixtures, vitamins, amino acids, antibiotics, and hormones.

The feed additive composition according to the present invention may be added to the feed of animals selected from the group consisting of pigs, cattle, chickens, goats, sheep, horses, fish, dogs and cats.

In the feed additive composition according to the present invention, the effective dose of fucosyllactose may be the same as that of the veterinary pharmaceutical composition, but may be less than the above range in the case of long-term intake for the purpose of health and hygiene or health control. Since there is no problem in terms of safety, the active ingredient is not limited to the above range and it can be used in an amount greater than the above range.

The dosage of the feed additive composition according to the present invention may be appropriately adjusted by those skilled in the art depending on the type of animal to which the composition is administered, the age of the animal, the weight of the animal, the disease to be prevented, the desired effect, and the like.

As used herein, the term "viral infection" includes symptoms caused by viral infection or diseases caused by viral infection.

Meanwhile, as can be seen from the following experiment, 2'-FL and 3-FL have antiviral activity, and thereamong, 3-FL is found to have significant antiviral activity and inhibitory activity against viral infection compared to 2'-FL in vitro (confirmation of improvement in cell-specific antiviral activity and resistance to broad-spectrum viruses) and in vivo (confirmation of improvement in resistance to viral infection in a mouse model).

In particular, conventional research reported that NO is known as a physiologically active substance having antiviral activity against various viruses (Fabio Lisi et al., 2021, ADVANCED SCIENCE, 8, 2003895; Mark R. Garren et al., 2021, Appl Mater Today, 22, 100887) and attempts are thus being made to develop various therapeutic agents. However, NO is always overproduced as a reactive oxygen species and causes toxicity to cells. In the present invention, 3-FL causes overproduction of NO (about 4 times compared to the control) only when viral infection occurred. The cells itself lead to an increase in the production of NO that can respond to viral infection, suggesting that 3-FL can assist in resistance against infection with various types of viruses, without limitation to influenza virus.

In addition, it was identified by the present invention that the corona-pseudovirus, the model virus, was found to have excellent resistance to viral infection upon ingestion and culture of 3-FL. Pseudovirus is widely used to study antiviral agents, serums, vaccines, antibody treatments and the like, rather than to directly target viruses with high biological safety ratings, and it is known to obtain the same results as real viruses (Ou x et al., 2020, Nat Commun 11, 1620; Nie J et al., 2020, Nat protoc 15, 3699-3715; Condor Capcah J M et al., 2020, Front Cardiovasc Med 7, 618651). Therefore, the 3-FL of the present invention is highly effective in improving resistance to a wide spectrum of viruses and is thus utilized in various antiviral applications.

Hereinafter, the present invention will be described in more detail with reference to the following Example. The Example is provided only for detailed description of the present invention and those skilled in the art will appropriate that the scope of the present invention is not limited to Example.

EXAMPLE 1

Confirmation of In Vitro Antiviral Effects of 2'-fucosyllactose (2'-FL) or 3-fucosyllactose (3-FL)

1-1. Antiviral Efficacy against Influenza Virus Infection through Cell Experiments 1-1-1. Suppression of Viral Infection Depending on 2'-FL or 3-FL Administration Period MDCK cell cultures were treated with 2'-fucosyllactose (2'-FL) or 3-fucosyllactose (3-FL), allowed to be adapted thereto well, infected with influenza virus, and then subjected to plaque reduction assay to determine the antiviral activity of 2'-FL or 3-FL against influenza virus (a of FIG. 1).

Specifically, MEM medium of MDCK was treated with each of 1 or 10 g/L of 2'-FL and 0.1 or 1 g/L of 3-FL, respectively, and then cultured for 0 to 3 passages. Then, the medium was removed, the residue was washed with PBS, and experimental groups were infected with the same amount of influenza H1N1 virus. 72 hours later, a plaque reduction assay was performed.

72 hours later, formation of plaques was observed. The result showed that the experimental group treated with 2'-FL did not exhibit a reduction in plaque formation, regardless of the concentration of the treated 2'-FL or the number of passages treated (b of FIG. 1). On the other hand, among the experimental groups including the culture medium treated with 0.1 g/L of 3-FL, the experimental group treated for 3 passages exhibited a reduction in plaque formation of about 70% compared to the experimental group treated for 0 passages. The experimental groups treated with 1 g/L of 3-FL exhibited a reduction in plaque formation in proportion to the number of passages. The experimental group treated for 1 passage formed 80% of a plaque area and the experimental group treated for 2 passages formed 50% of a plaque area, compared to the experimental group treated for 0 passages. In particular, the experimental group treated with 3-FL for 3 passages exhibited a great reduction in viral infection corresponding to about 35% of the plaque area compared to the experimental group treated with 3-FL for 0 passages.

In addition, the efficacy of inhibiting viral infection of 3-FL culture was determined using cytopathic effect (CPE) reduction assay. Specifically, MDCK cells were measured in a culture medium supplemented with 0.1 or 1.0 g/L of 2'-FL or 3-FL for 0, 1 and 3 passages and then treated with a medium diluted with the same amount of H1N1 influenza virus. After culture for 18 hours, dead cells caused by virus infection were removed, and live cells were fixed by treatment with formaldehyde and stained with crystal violet. Then, the cell-stained crystal violet was dissolved in methanol and then the absorbance of the dissolved crystal violet was measured using a spectrophotometer. The cytopathic effect (CPE) reduction was calculated based on 0% and 100%, the absorbance of the dissolved crystal violet when treating the same number of MDCK cells not treated with PBS or fucosyllactose with Oriental H1N1 virus dilution or culture solution, and then culturing the cells for 18 hours. The result of the cytopathic effect reduction assay showed that MDCK cells cultured by treatment with PBS or 2'-FL did not exhibit a great cytopathic effect reduction, regardless of the concentration and the number of passages of the culture, but culture after treatment with 3-FL at 0.1 g/L showed about a viral infection inhibition of 70% for culture for 3 passages, and cultures after treatment with 1.0 g/L 3-FL for 1 and 3 passages exhibited high viral infection inhibitions of about 30% and 75%, respectively (c of FIG. 1).

This indicates that the enhancement of the ability to resist viral infection upon 3-FL administration, which was observed in the animal experiment (Example 2 below), also occurred even at the cellular level.

1-1-2. Confirmation of Antiviral Mechanism Depending on Administration of 2'-FL or 3-FL The virus was directly treated with fucosyllactose and the antiviral activity was then measured to determine whether the antiviral activity obtained by the administration of fucosyllactose as described earlier is due to the fact that fucosyllactose binds to the virus to directly inhibit the binding to host cells, or the cells themselves have an improved ability to fight viral infection.

Figure 2:
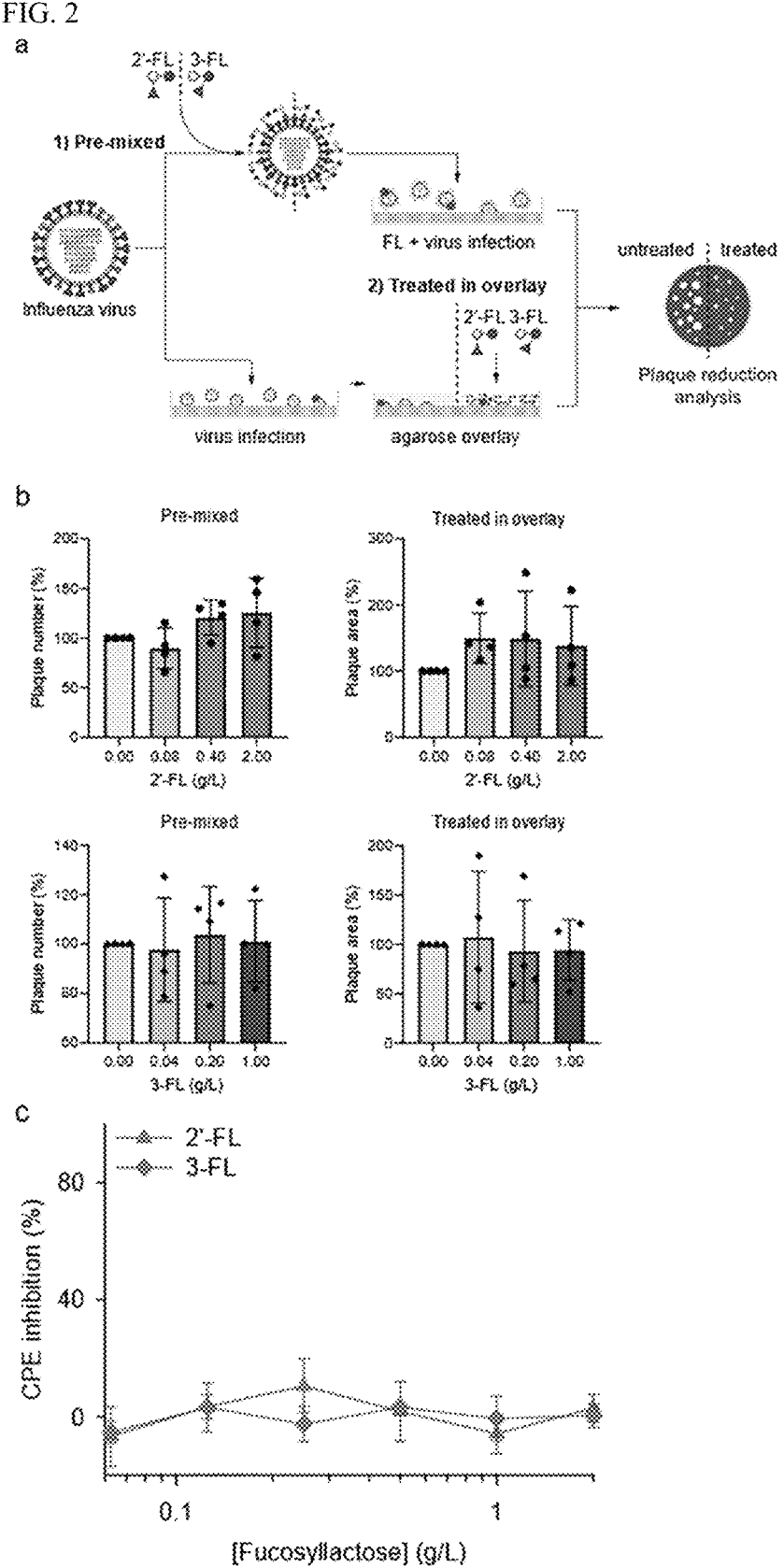
FIG. 2 is a schematic diagram illustrating two methods of plaque reduction assay to determine the antiviral activity after directly treating influenza virus with fucosyllactose and performing reaction (a), the result thereof (b), and the result of a cytopathic effect reduction assay (c)

For this purpose, two methods, namely, plaque formation reduction and cytopathic effect reduction assays were performed: first method) a method of reacting a virus solution with fucosyllactose, followed by treatment of MDCK cells therewith; and second method) a method of injecting with H1N1 influenza virus, followed by treatment with a 1% agarose overlay medium treated with fucosyllactose (a of FIG. 2).

Specifically, in the first method, influenza virus was treated with 0.08, 0.4, and 2 g/L of 2'-FL or 0.04, 0.2 and 1 g/L of 3-FL, followed by reaction at 37° C. for 1 hour. Then, the MDCK cells washed with PBS were infected with the result and treated with a general 1% agarose overlay medium, and plaque formation was induced for 72 hours.

In the second method, MDCK cells washed with PBS were infected with the same amount of H1N1 virus, and a 1% agarose overlay medium was treated with fucosyllactose, followed by culture for 72 hours to perform a plaque reduction assay. At this time, the 1% agarose overlay medium was treated with 2'-FL at a concentration of 2, 0.4, or 0.08 g/L or with 3-FL at a concentration of 1, 0.2, or 0.04 g/L and the infected cells were treated with the result.

In the third method, using a cytopathic effect reduction assay, a mixture of virus and fucosyllactose was prepared by diluting 2'-FL or 3-FL in the same concentration of H1N1 virus by ½ from a maximum of 2.0 g/L, and was cultured at 37° C. for 1 hour and MDCK cells were treated with the result. After 18 hours, a reduction in cytopathic effect was measured as in Example 1-1-1.

Antiviral activity of fucosyllactose could not be observed with the above three methods (b and c of FIG. 2). This means that there is a mechanism other than the direct mechanism by which fucosyllactose acts directly on the virus to inhibit the activity of viral proteins or acts on cellular proteins to inhibit the interaction with the virus. In consideration thereof in combination with the results of FIG. 1, 3-FL enhances the ability of cells to fight viral infection as well as the ability to act on cells for a long period of time.

Figure 3:
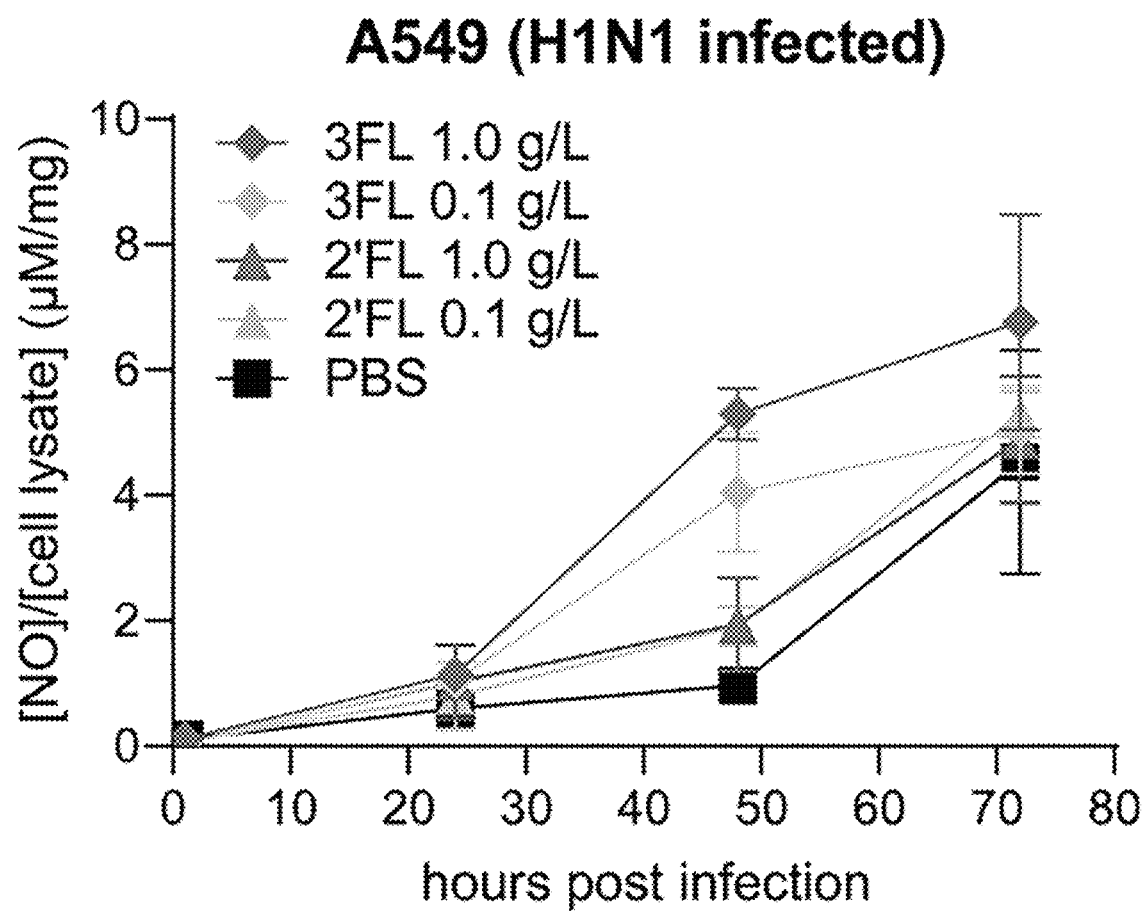
FIG. 3 shows a result of comparison in production of nitric oxide (NO), an antiviral substance, through infection of fucosyllactose with an influenza virus using A549 cells.
Figure 4:
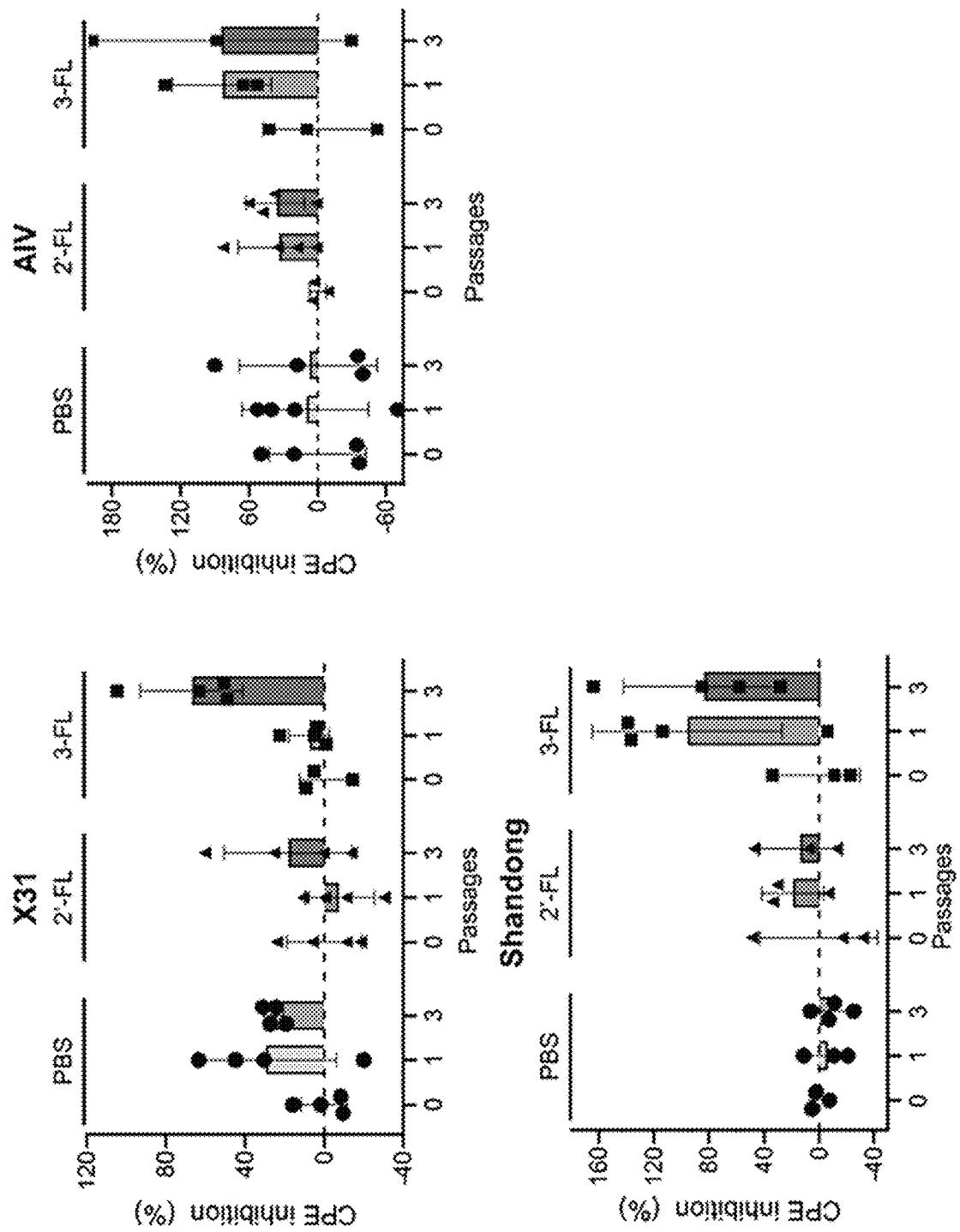
FIG. 4 is an experimental result confirming the antiviral effect of fucosyllactose against a broad spectrum of viral infections, namely, against H3N2 (X31), H5N2 (AIV), and influenza B virus (IBV; Shandong)
Figure 5:
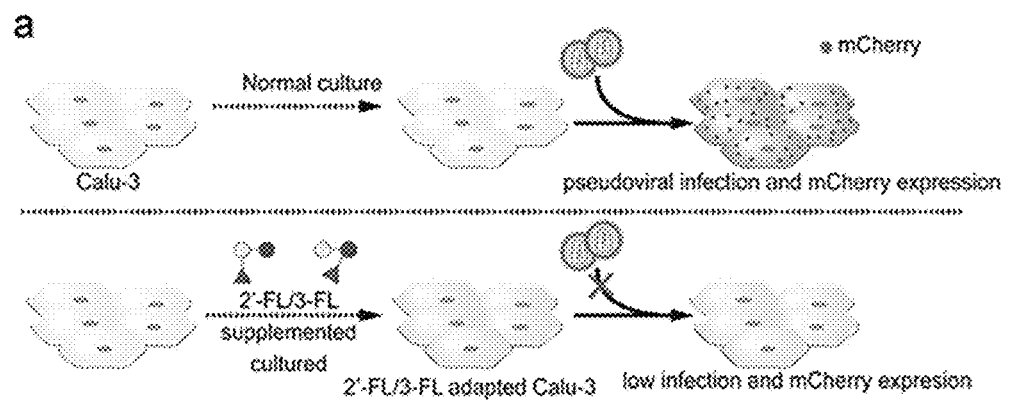
FIG. 5 is a schematic diagram illustrating an experimental procedure for determining an antiviral effect of fucosyllactose against corona-pseudovirus (a), luciferase activity of corona-pseudovirus and fluorescence after fluorescent protein expression (b), and the result confirming the degree of inhibition against the corona-pseudovirus infection depending on the drug concentration (c)
Figure 5:
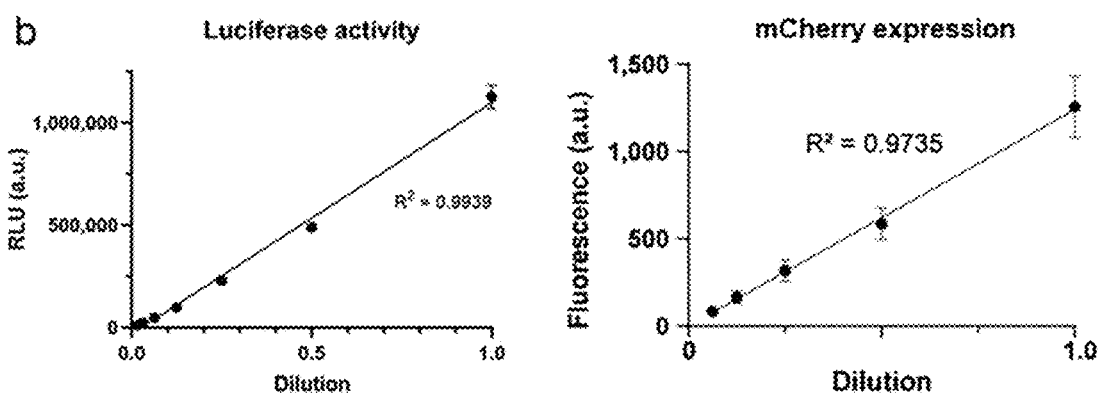
Figure 5:
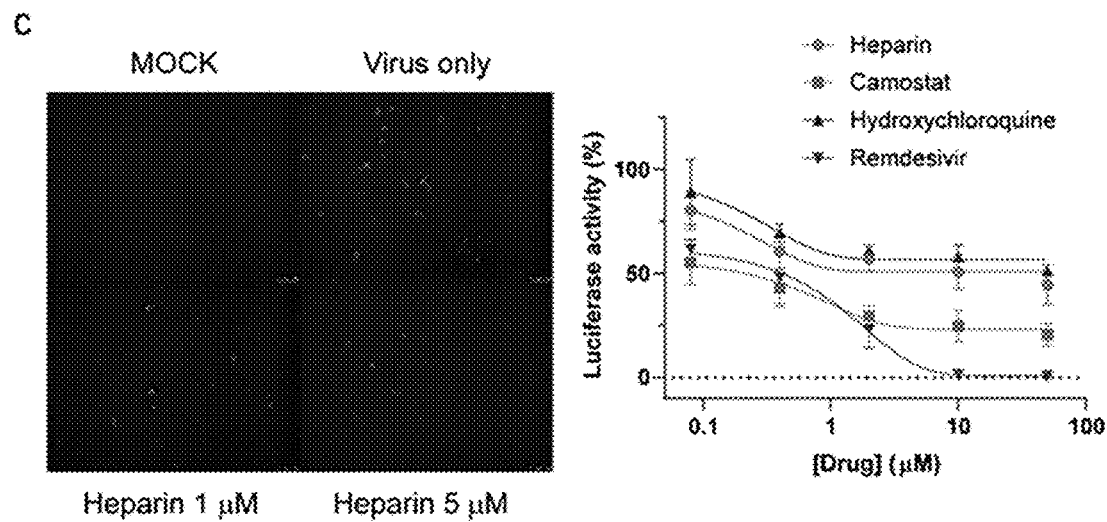

1-1-3. Increased Intrinsic Antiviral Capacity of Cells before Viral Infection or Administration of 2'-FL or 3-FL In order to determine the basis on which 3-FL increases the resistance of the cells to viruses, the overproduction of nitric oxide (NO) was investigated as one of various experiments. Like MDCK cells, lung cells, fucosyllactose was administered to A549 cells, followed by culturing. Influenza virus infection was performed, and the production of nitric oxide (NO), an antiviral substance, was compared. Fucosyllactose was added at 0.1 or 1.0 g/L to the culture medium, culturing was performed for 3 passages, the result was infected with H1N1 influenza virus, the infection medium was collected at 1, 24, 48 and 72 hours, and a NO concentration was measured (FIG. 3).

Figure 6:
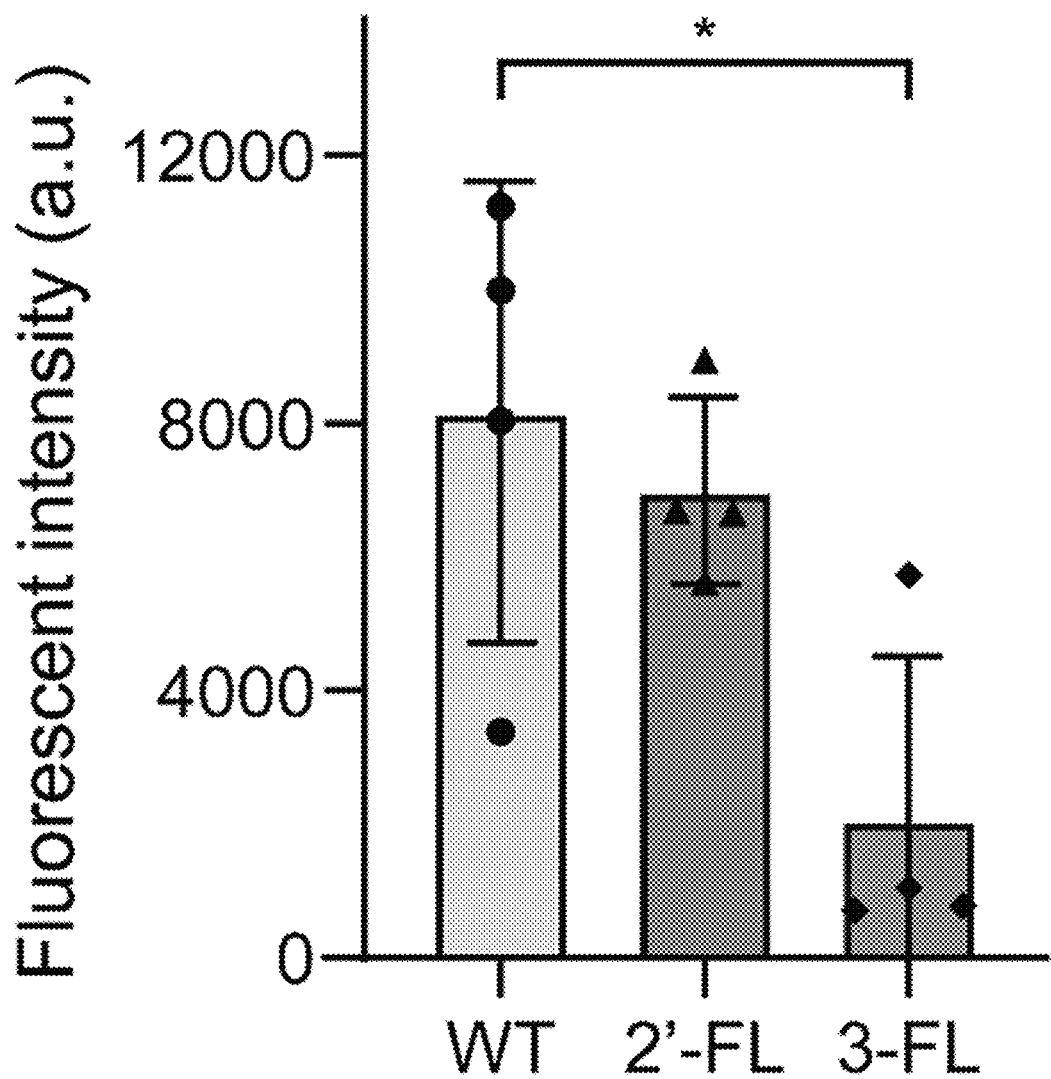
FIG. 6 shows the fluorescence of corona-pseudovirus measured to determine the antiviral effect of fucosyllactose against corona-pseudovirus.

Although there was no great change at 1 hour, the NO concentration slightly increased after 24 hours, and the cells passage-cultured at 1.0 g/L of 3-FL in the medium collected at 48 hours had an about 3.9-fold higher NO concentration than that of the experimental group treated with PBS. The reported literature showed that NO is involved in muscle relaxation, vasodilation, mucus secretion, and proliferation of immune-related cells, as well as inhibitory activity against viral replication and virus inactivation. In addition, it has been reported that NO has the ability to inhibit infection by various types of viruses such as Coronaviridae, Picornaviridae, Orthomyxoviridae, Flaviviridae, Retroviridae, and Herpesviridae (Fabio Lisi et al., 2021, Nitric Oxide to Fight Viral Infections, ADVANCED SCIENCE, 8, 2003895; Mark R. Garren et al., 2021, Nitric oxide and viral infection: Recent developments in antiviral therapies and platforms, Appl Mater Today, 22, 100887). Since NO is a physiologically active substance that exhibits antiviral activity against various viruses, it is developed as a therapeutic agent for various viruses, including a therapeutic agent for coronavirus. That is, attempts are being made to develop a broad-spectrum active antiviral agent through a method of directly spraying NO to the lungs or tissues in which the virus has invaded, a method of spraying a substance inducing NO to a target tissue, and the like.

However, NO, as a reactive oxygen species, may be toxic to cells if it is constantly overproduced. Very surprisingly, 3-FL effectively inhibits the penetration of the virus by making the cells produce NO in an excess of about 4 times compared to the control group, when infected with the virus. However, 3-FL has no effect on the concentration of NO which is continuously produced by cells, despite treatment for 3 passages, unless there is viral infection. This is the most ideal property for researchers who intend to develop NO as a broad spectrum active antiviral agent. That is, 3-FL increases the production of NO that leads to cell's own resistance to viral infection during viral infection. This increase in NO production means that 3-FL can resist infection with various types of viruses, without limitation to influenza virus.

The two results of 1-1-2 and 1-1-3 indicate that the concentration and passage-dependent antiviral activity of 3-FL, as determined from the previous results, does not result from simply acting on the virus to inhibit the ability to infect cells, but from improving the inherent resistance of cells to viruses.

1-2. Confirmation of Antiviral Activity of 2'-fucosyllactose or 3-fucosyllactose against Various Types of Animal Cells and Broad-Spectrum Virus 1-2-1. Increased Ability to Resist Broad-Spectrum Viral Infections upon Administration of 2'-FL or 3-FL In order to verify that the effect of the ability of 2'-FL or 3-FL to resist viral infection as determined previously is not limited to one type of virus, cytopathic effect reduction assay was performed using various influenza viruses of strains.

The cytopathic effect reduction assay was performed in the same manner as in Example 1-1-1, except that the medium diluted with H3N2 (X31), H5N2 (AIV) or Influenza B virus (IBV; Shandong) was treated during virus infection. After culturing for 18 hours, dead cells caused by viral infection were removed, live cells were fixed and stained, and then absorbance was measured. In all cells infected with X31, AIV and Shandong strains, 3-FL-dependent improvement in cell viability was identified. MDCK cells after treatment with PBS or 2'-FL and culturing showed only an improvement in cell viability of less than 30%, whereas MDCK cells treated with 3-FL and then cultured showed a much higher 80% cytopathic effect reduction upon infection with three influenza strains (FIG. 4).

This suggested that the antiviral activity obtained by 3-FL administration is an inhibitory activity against broad-spectrum viral infection capable of inhibiting a common cellular infection for viruses, not against a limited range of viral infection.

1-2-2. Improvement of Anti-Corona-Pseudovirus Efficacy of Calu-3 Cells upon Administration of 2'-FL or 3-FL SARS-CoV-2 spike encoding plasmid and HIV gag-pol-reporter plasmid, NL4.3-mCherry-Luciferase, were co-transfected into a HEK293T cell line to produce corona-pseudovirus. The produced corona-pseudovirus has a structure in which SARS-CoV-2 spike glycoprotein is incorporated into the membranes of viral particles composed of HIV structural proteins and, when infected into target cells, mCherry-Luciferase genes contained in the virus particles are delivered to and expressed in the target cells and whether or not infection occurs and the efficacy of the treated drug can be determined through the expression levels of the expressed fluorescent/luminescent proteins (a of FIG. 5). Pseudovirus is widely used to study antiviral agents, serums, vaccines, antibody treatments and the like, rather than to directly target viruses with high biological safety ratings, and it is known to obtain the same results as real viruses (Ou x et al., 2020, Nat Commun 11, 1620; Nie J et al., 2020, Nat protoc 15, 3699-3715; Condor Capcah J M et al., 2020, Front Cardiovasc Med 7, 618651).

In order to prove the suitability of the prepared corona-pseudovirus as a virus infection model, HEK-293T cells expressing ACE2 and TMPRSS2 proteins known to be recognized by SARS-CoV-2 were infected with corona-pseudovirus, and luciferase activity as a function of the dilution factor and the fluorescence upon expression of fluorescent proteins were measured. The result of the measurement showed that the luciferase activity expression as a function of dilution of the corona-pseudovirus and the fluorescence of the fluorescent protein decreased, and the degree of the expression was found to be highly correlated with the dilution factor (b of FIG. 5). In addition, heparin, Camostat, hydroxychloroquinine, and Remdesivir, which are known to have inhibitory activity against coronavirus, were treated with four types of drugs for corona-pseudovirus and the degree of infection was determined. The drugs act in different manners on the mechanism of coronavirus infection and thus have different degrees of inhibition against infection. However, infection with the corona-pseudovirus was inhibited in a concentration-dependent manner (c of FIG. 5). Accordingly, it was confirmed that infection with the corona-pseudovirus produced by the present inventors was found to be inhibited even with a well-known anti-coronavirus drug. This indicates that the corona-pseudovirus functions as a model virus.

In order to determine the antiviral activity of fucosyllactose against corona-pseudovirus, Calu-3 was passage-cultured by 4 passages in a culture medium containing 10 g/L of 2'-FL or 1 g/L of 3-FL and cultured, and the corresponding cells were infected with the prepared corona-pseudovirus to determine the efficacy of increasing resistance to viruses of 2'-FL or 3-FL.

The difference in infectivity of corona-pseudovirus using Calu-3 cells cultured for 4 passages using a culture medium supplemented with 3-FL was determined. The result showed that the Calu-3 passage-cultured for 4 passages had a fluorescence of about ¼ or less, compared to the control group passage-cultured in the normal culture medium (FIG. 6). However, there was no great difference between the fluorescence after infection of Calu-3 containing 2'-FL cultured for 4 passages with the corona-pseudovirus and the mCherry fluorescence of Calu-3 cells not containing fucosyllactose.

This means that the great enhancement of virus infection resistance by the 3-FL culture, which was observed during previous infection of MDCK cells with influenza virus, was the same as in the case of infection of different types of animal cells with a wide spectrum of viruses.

EXAMPLE 2

Figure 7:
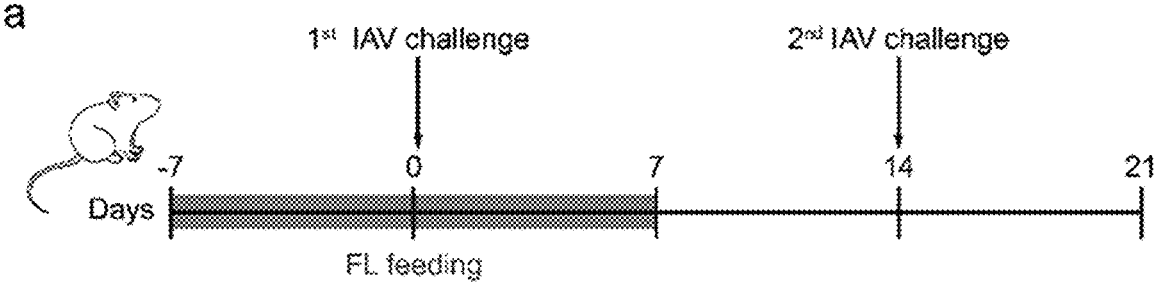
FIG. 7 is a schematic diagram illustrating a process for determining the antiviral effect by the administration of fucosyllactose to a mouse model (a), and changes in the weight change (b) and the survival rate (c) caused thereby.
Figure 7:
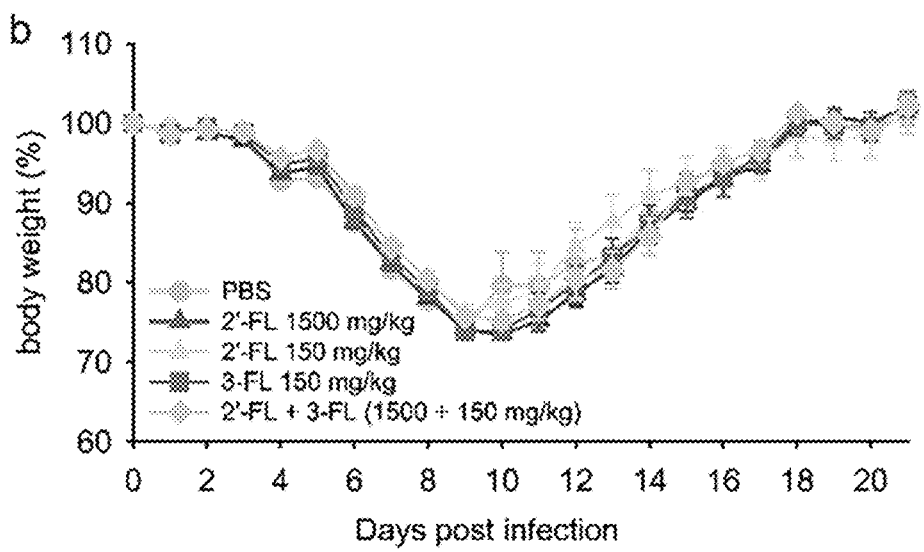
Figure 7:
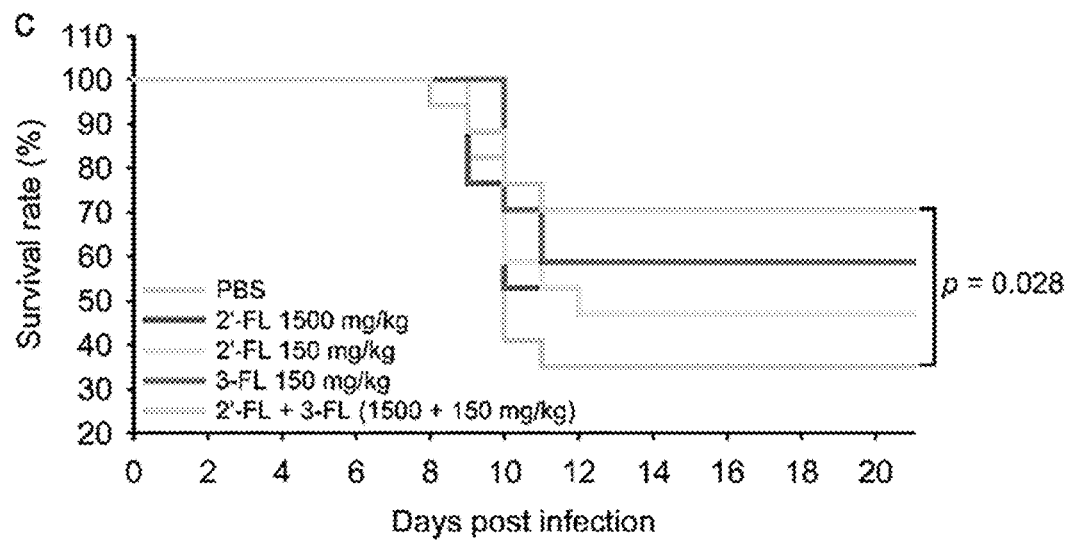

Confirmation of In Vivo Antiviral Effect of 2'-fucosyllactose or 3-fucosyllactose 2-1. Confirmation of Survival Rate in Mouse Model Animal Experiments after Fucosyllactose Administration and then Infection Antiviral activity after fucosyllactose administration was measured through mouse model animal experiments (FIG. 7A).

A control group administered PBS, and four experimental groups administered 2'-FL 1500 mg/kg, 2'-FL 150 mg/kg, 3-FL 150 mg/kg, and 2'-FL+3-FL (1500+150 mg/kg) were set, and 100 µl of PBS or a dilution of fucosyllactose in PBS was administered to 7-week-old mice (20 mice/each group) of the control group and the experimental groups once a day by gavage. The fucosyllactose administration was performed for a total of 14 days and primary infection was performed on the $7^{th}$ day after administration. The primary infection was performed by infecting the mouse with a 1 mouse lethal dose 50 (MLD5) of H1N1 influenza virus (H1N1; A/Puerto Rico/08/34) through intranasal administration and changes in body weight and survival rate were observed. 21 days after fucosyllactose administration, a secondary infection was performed by infection with a 10 MLD50 of H1N1 influenza virus.

After the primary infection, there was no great difference in the weight loss between each experimental group and the control group (b of FIG. 7), but there was a significant difference in survival rate therebetween. Only about 35% of mice in the control group survived after viral infection, whereas the experimental group administered 2'-FL exhibited a survival rate of about 45%, regardless of the concentration. However, it was confirmed that the two experimental groups administered 3-FL exhibited greatly ameliorated infection symptoms and final survival rates of 60% (3-FL 150 mg/kg) and 70% (2'-FL+3-FL (1500+150 mg/kg)), respectively (c of FIG. 7).

This indicates that the administration of 3-FL can enhance the ability of mice to resist viral infection. In addition, single administration of 2'-FL did not exhibit sufficient resistance to virus infection, whereas administration of 3-FL in combination with 2'-FL exhibited a synergistic effect of significantly increasing the survival rate.

This indicates that 3-FL enhances the biological ability to fight viral infection through a mechanism different from 2'-FL, and does not interfere with the previously reported immune-enhancing efficacy based on 2'-FL T-cell proliferation enhancement.

As is apparent from the foregoing, it was found in the present invention that 2'-fucosyllactose and 3-fucosyllactose, which are human milk oligosaccharides (HMOs), have antiviral activity, and in particular, 3-fucosyllactose exhibits in vitro and in vivo much higher antiviral activity and inhibitory activity against viral infection compared to 2'-fucosyllactose and is thus useful as an antiviral agent.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating a viral infection, comprising administering a composition comprising 3-fucosyllactose as an active ingredient to a subject in need thereof,
   wherein the viral infection is an infection with coronavirus.

2. The method according to claim 1, wherein the composition further comprises 2'-fucosyllactose.

* * * * *